(12) United States Patent
McDonald

(10) Patent No.: US 8,790,031 B2
(45) Date of Patent: Jul. 29, 2014

(54) ANTISEPTIC APPLICATOR

(75) Inventor: James P. McDonald, El Paso, TX (US)

(73) Assignee: Carefusion 2200, Inc., San Diego, CA (US)

( * ) Notice: Subject to any disclaimer, the term of this patent is extended or adjusted under 35 U.S.C. 154(b) by 369 days.

(21) Appl. No.: 12/961,255

(22) Filed: Dec. 6, 2010

(65) Prior Publication Data

US 2012/0141186 A1 Jun. 7, 2012

(51) Int. Cl.
*A61M 35/00* (2006.01)
(52) U.S. Cl.
CPC .................................. *A61M 35/003* (2013.01)
USPC ............... 401/133; 401/132; 401/145; 604/3
(58) Field of Classification Search
USPC ............... 604/3; 401/132, 133, 134, 135, 145
See application file for complete search history.

(56) References Cited

U.S. PATENT DOCUMENTS

| | | | |
|---|---|---|---|
| 1,417,082 A * | 5/1922 | McNamara ................... 401/152 |
| 3,757,782 A | 9/1973 | Aiken | |
| 3,759,259 A * | 9/1973 | Truhan ............................... 604/3 |
| 4,415,288 A | 11/1983 | Gordon et al. | |
| 4,498,796 A | 2/1985 | Gordon et al. | |
| 4,578,055 A * | 3/1986 | Fischer ............................. 604/2 |
| 4,784,506 A * | 11/1988 | Koreska et al. ............... 401/132 |
| 4,925,327 A * | 5/1990 | Wirt ............................... 401/205 |
| 5,288,159 A | 2/1994 | Wirt | |
| 5,308,180 A | 5/1994 | Pournoor et al. | |
| 5,435,660 A | 7/1995 | Wirt | |
| 5,445,462 A | 8/1995 | Johnson et al. | |
| 5,658,084 A | 8/1997 | Wirt | |
| 5,769,552 A | 6/1998 | Kelley et al. | |
| 5,772,346 A | 6/1998 | Edwards | |
| 5,791,801 A | 8/1998 | Miller | |
| 5,927,884 A | 7/1999 | Kao | |
| 6,371,675 B1 | 4/2002 | Hoang et al. | |
| 6,488,665 B1 | 12/2002 | Severin et al. | |
| 6,910,822 B2 * | 6/2005 | Hidle et al. ................... 401/134 |
| 6,916,133 B2 | 7/2005 | Hoang et al. | |
| 7,201,525 B2 | 4/2007 | Mohiuddin | |
| 7,866,907 B2 * | 1/2011 | Cable et al. ................... 401/134 |
| 7,993,066 B2 * | 8/2011 | Flores et al. ................... 401/134 |
| 2006/0018701 A1 * | 1/2006 | Mohiuddin ................... 401/132 |
| 2006/0039742 A1 | 2/2006 | Cable, Jr. et al. | |
| 2007/0248399 A1 * | 10/2007 | Tufts et al. ................... 401/133 |

* cited by examiner

*Primary Examiner* — David Walczak
*Assistant Examiner* — Joshua Wiljanen
(74) *Attorney, Agent, or Firm* — Arent Fox LLP

(57) ABSTRACT

An applicator assembly may include body having a proximal end portion and a distal end portion, a container having a closed proximal end, an interior, and an open distal end, wherein the container is coupled to the proximal end portion, a material bonded to the open distal end and sealing the interior of the container, and an application member attached to the distal end portion, wherein the interior of the container is placed in fluid communication with the application member by way of a compressive force applied along circumferential areas toward the distal end of the container. A method of manufacturing an applicator for applying a solution to a surface is provided.

22 Claims, 6 Drawing Sheets

ANTISEPTIC APPLICATOR

BACKGROUND

1. Field

The present disclosure relates to an antiseptic applicator and method of use thereof, and more particularly, to an antiseptic applicator that uses a compressive force to actuate release of a sealed solution, preferably an antimicrobial solution, from a cartridge type container without puncturing or fracturing the container.

2. Description of Related Art

Antiseptic applicators for the preparation of a patient prior to surgery, for example, are known and common in the prior art. Conventional applicators rely on various means of actuation to release a self-contained reservoir of antimicrobial solution for sterilization of the patient's skin. For example, a number of applicators are designed with a puncturing means. These applicators typically include a head with a spike, for example, and a sealed container or cartridge. A push or screw motion is employed to axially translate the head toward the sealed container so that the spike may pierce the sealed container and effectuate the release of the solution contained therein. Some examples of applicators using a puncturing means include U.S. Pat. Nos. 4,415,288; 4,498,796; 5,769,552; 6,488,665; and 7,201,525; and U.S. Pat. Pub. No. 2006/0039742.

Other conventional applicators rely on breaking an internally situated frangible container or ampoule through the application of a one-way directional force or a localized application of pressure. The directional force is typically applied longitudinally to one end of the ampoule by a pushing motion designed to force the ampoule to break under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,658,084; 5,772,346; 5,791,801; 5,927,884; 6,371,675; and 6,916,133.

The conventional applicators have been developed to include shaped walls having inward projections that engage the periphery of the ampoule to maintain the ampoule within the cavity and to prevent untoward movement of shards of glass through an applicator member when fracturing of the ampoule is effected. Further, applicators have been developed with shaped walls presenting a region to be grasped and squeezed by the user which provide a fulcruming effect so that the user squeezes the shaped wall at a location that is not directly in contact with the ampoule. In other words, the ampoule is fractured at a location that is spaced from the portion of the wall that is squeezed by the user, protecting the user from shards of the ampoule projecting through the wall. However, the possibility still exists that a user will over-squeeze the shaped wall, causing extreme fracturing of the frangible ampoule, and resulting in shards or pieces of glass, for example, penetrating through the applicator member. Although such liquid applicators represent an improvement over earlier conventional devices, there is a need to provide a liquid applicator that reduces or preferably eliminates the risk of the user being injured by shards of glass or glass particles penetrating the applicator member.

SUMMARY

In accordance with certain aspects of the present invention, an applicator assembly may include body having a proximal end portion and a distal end portion, a container having a closed proximal end, an interior, and an open distal end, wherein the container is coupled to the body, a material bonded to the open distal end and sealing the interior of the container, and an application member attached to the distal end portion, wherein the interior of the container is placed in fluid communication with the application member by way of a compressive force applied along circumferential areas toward the distal end of the container.

In accordance with another certain aspect of the present invention, the body of the applicator assembly may include a release mechanism, wherein the release mechanism applies the compressive force in response to an activation force applied longitudinally against the proximal end of the container. In accordance with another certain aspect of the present invention, the release mechanism may include at least one wedge arranged on an interior surface of the body.

In accordance with yet another certain aspect of the present invention, the body of the applicator assembly may include a retaining mechanism that resists separation of the container from the body. The retaining mechanism may comprise a tapered configuration of the proximal end portion.

In accordance with another certain aspect of the present invention, the body of the applicator assembly may include a middle body portion connecting the proximal end portion and the distal end portion, the middle body portion having thicker walls than the proximal end portion and housing the distal end of the container.

In accordance with yet another certain aspect of the present invention, the application of the compressive force creates a tensile stress in the bond which ruptures the seal along circumferential areas of the distal end substantially perpendicular to the circumferential areas of the applied compressive force.

In accordance with another certain aspect of the present invention, a method of manufacturing an applicator for applying a solution to a surface includes providing a container having a closed proximal end, an interior receptacle, and an open distal end; filling the container with the solution to be applied; bonding a sealing material to the open distal end of the container to seal the solution in the interior receptacle of the container; providing an applicator body having a proximal end portion and a distal end portion; coupling an application material to the distal end portion; and coupling the container to the proximal end portion, wherein application of a compressive force on the distal end of the container ruptures the sealing material bond and allows the solution to flow through the body to the application material.

It will become readily apparent to those skilled in the art from the following detailed description, wherein it is shown and described only exemplary configurations of a an applicator assembly. As will be realized, the invention includes other and different aspects of an applicator and assembly and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Figure 1A:
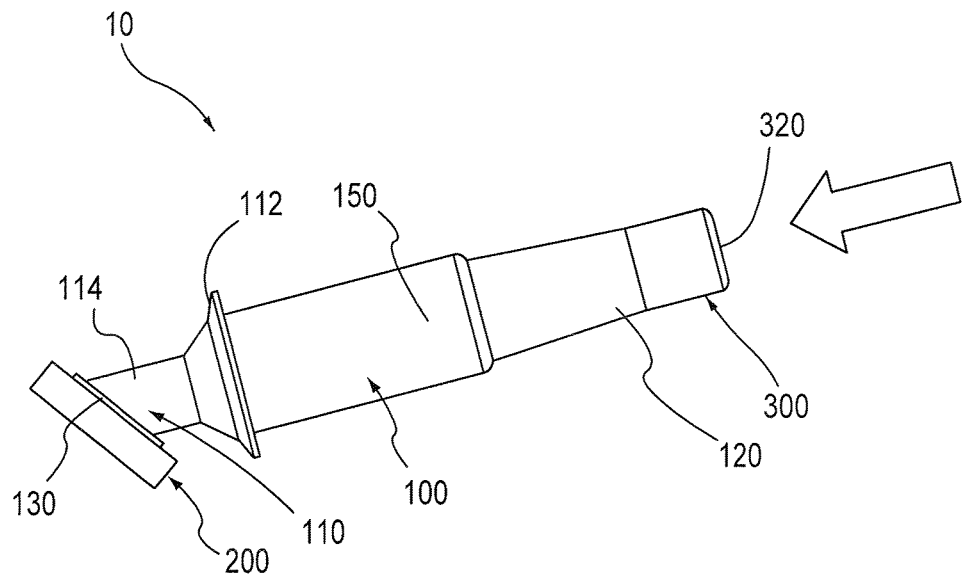
FIG. 1A is a perspective view of an antiseptic applicator, in accordance with certain aspects of the present invention.

Various aspects of an antiseptic applicator may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of an antiseptic applicator in addition to the orientation depicted in the drawings. By way of example, if an antiseptic applicator in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of an antiseptic applicator disclosed herein.

Figure 1B:
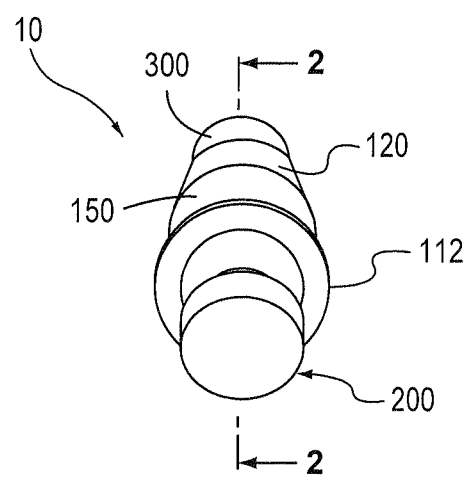
FIG. 1B is a perspective longitudinal end view of the antiseptic applicator of FIG. 1A, in accordance with certain aspects of the present invention.
Figure 2:
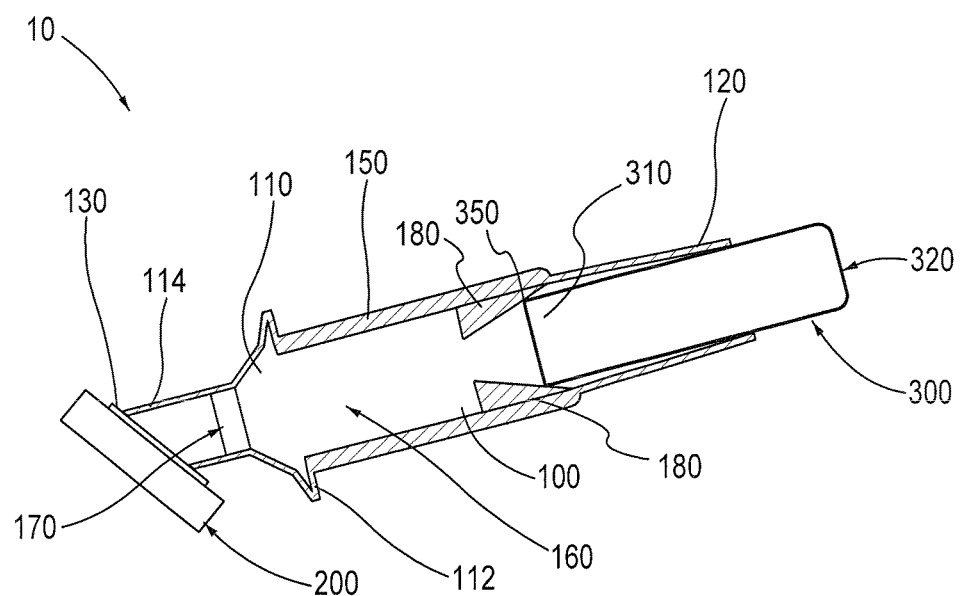
FIG. 2 is a sectional view of the antiseptic applicator shown in FIGS. 1A and 1B, in accordance with certain aspects of the present invention.

The antiseptic applicator may be compact and ergonomically designed. As shown in FIGS. 1A, 1B and 2, an antiseptic applicator 10 may comprise a substantially hollow body 100, which may be cylindrical in shape, an application member 200 mounted to a distal end portion 110 of the body 100, and a solution container 300 slidably received by a proximal end portion 120 of the body 100. The solution container 300 may be cylindrical in shape to position a distal end 310 concentrically into the body 100. A proximal end 320 may extend beyond the proximal end portion 120 of the body 100, or it may be sized to lie completely within the body 100 or extend to the proximal end portion 120.

The application member 200 may be formed from a foam sponge material, for example, or any suitable material that allows the controlled application of the contained solution from the solution container 300 to a surface external to the applicator 10. The material chosen may be porous with a particular soak rate, for example, or may be provided with structural features, including slits or apertures, to direct and control the flow rate of the solution through the application member 200. The body 100 may be configured to have a mounting flange 130 at the distal end portion 110. The mounting flange 130 provides a surface for affixing the application member 200 to the body 100.

The solution container 300 is preferably a self-contained structure, formed of a suitable material, such as a high-density polyethylene plastic, that is flexible, yet resistant to permanent deformation and chemical leeching. The container 300 may be filled with various liquids such as antiseptics or medicaments, chemical compositions, cleansing agents, cosmetics, or the like, and preferably an antimicrobial liquid or gel composition, such as a chlorhexidine gluconate solution or a povidone iodine (PVP-I) alcohol gel solution, for antiseptic application to a patient prior to surgery. The container 300 is designed to withstand various heat and chemical sterilization techniques, which may be performed sequentially with a solution filling process, in accordance with techniques that are well known in the art.

Figure 4:
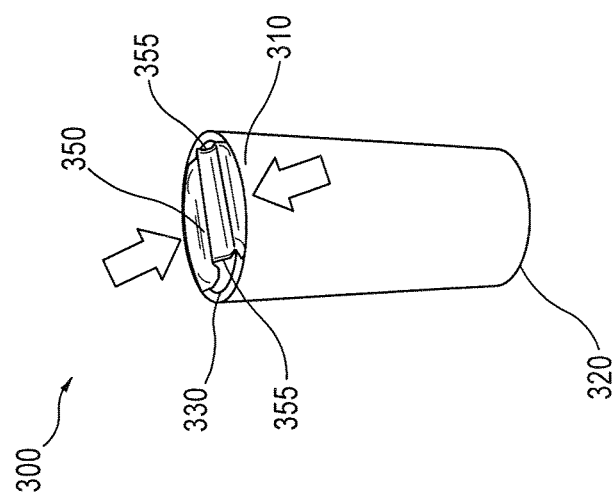
FIG. 4 is a perspective view of a distal end of an exemplary container, in accordance with certain aspects of the present invention.
Figure 3:
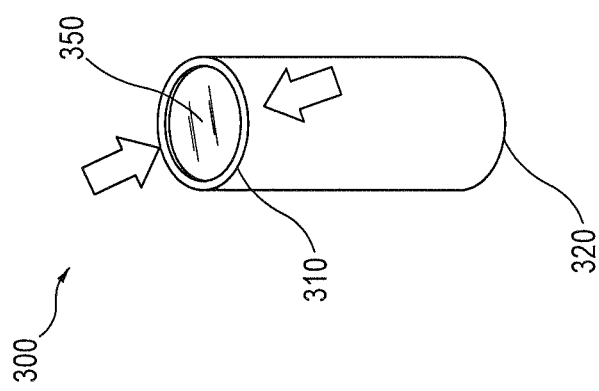
FIG. 3 is a perspective view of a distal end of an exemplary container, in accordance with certain aspects of the present invention.

As shown in FIGS. 3 and 4, the container 300 may be sealed at the distal end 310 with a sealing material 350, such as a thin plastic or an aluminum foil, for example. The sealing material 350 may be bonded to the container 300 about a periphery of a container opening 330 so that the solution contained therein is sealed from any external contamination. The material properties and/or configuration of the sealing material 350, as well as the type and strength of the bond between the sealing material 350 and the container 300, may be such that application of substantially opposing compressive forces (i.e., a pinching or clamping force), applied toward the distal end 310 of the container 300, may force a tearing of the sealing material 350 and/or a separation of the sealing material 350 from the container 300.

As shown in FIGS. 3 and 4, as the container 300 is subjected to an increased inward deformation in the circumferential areas of applied compressive force (represented by the arrows), the container 300 is subjected to increased outward deformation in the circumferential areas perpendicular to the applied compressive force. The increased outward deformation creates an increased tensile stress in the circumferential areas perpendicular to the applied compressive force until the tensile stress overcomes the material properties of the sealing material 350 and/or the bond of the sealing material 350 to the container 300. Various features, including, for example, a thickness of the sealing material 350, surface scoring provided on a surface of the sealing material 350 to create points of weakness for a planned separation, and/or the type and strength of the sealing bond, such as whether the bond is formed by a heat sealing technique and/or formed using an adhesive, may determine the level and/or location of applied compressive force required to open the seal and allow fluid communication through the container opening 330.

Figure 5A:
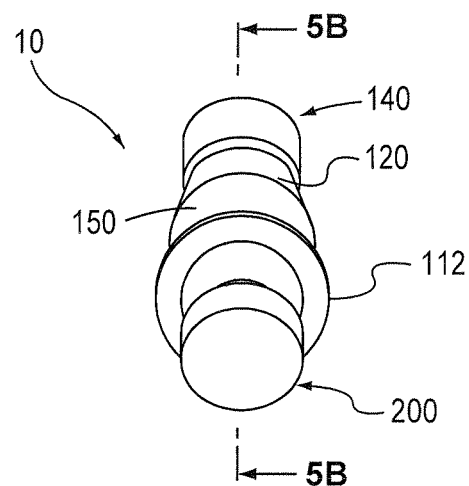
FIG. 5A is a perspective longitudinal end view of an antiseptic applicator, in accordance with certain aspects of the present invention.
Figure 5B:
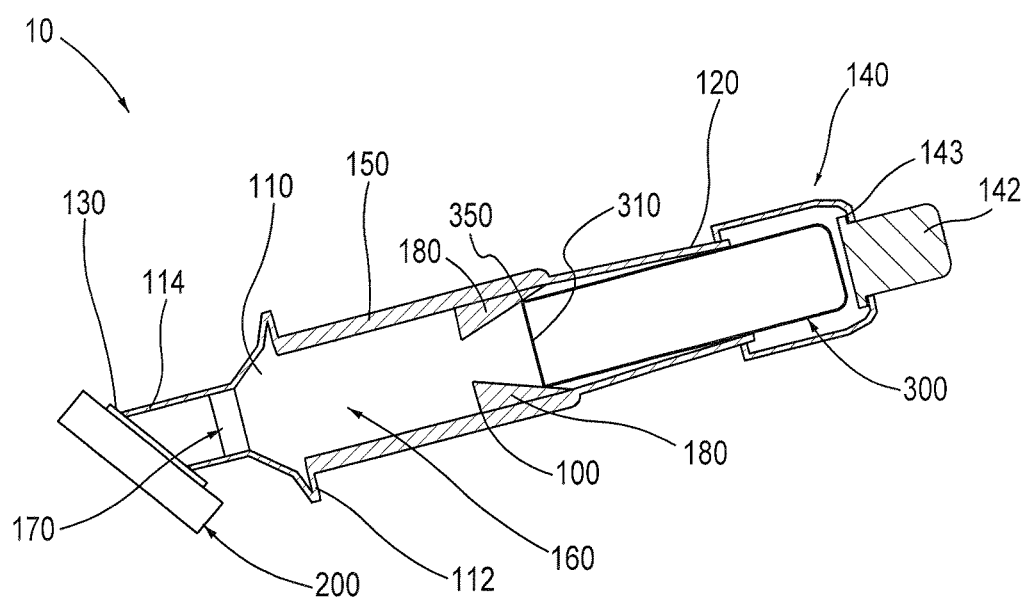
FIG. 5B is a sectional view of the antiseptic applicator of FIG. 5A, in accordance with certain aspects of the present invention.

The body 100 of the applicator may be formed with the proximal end portion 120 and the distal end portion 110 separated by a middle body portion 150. An optional retaining mechanism may be provided, for example, toward the proximal end portion 120, for coupling or retaining the container 300 to/in the body 100 and to prevent the container from sliding out of the body 100 in a proximal direction. For example, as shown in FIGS. 1A and 2, the proximal end portion 120 may be configured to taper from the middle body portion 150 toward the proximal end of the body 100 so as to abut an outer surface of the container 300. The tapered proximal end portion 120 may thus provide a holding resistance against the container 300 to retain the container from sliding out of the body 100. In accordance with another aspect of the present invention, any suitable retaining mechanism, such as an adhesive bond or a tab and slot connection, for example, may be used to retain the container 300 in the body 100 while permitting translation toward the distal end 110 by application of an applied force on the proximal end 320 of the container 300. According to yet another aspect of the present invention, as shown in FIGS. 5A and 5B, a retaining cap 140 may be provided at the proximal end portion 120 of the body to completely enclose the container within the body 100. A plunger 142 having a retaining flange 143, for example, may be slidably mounted through the retaining cap 140 to abut a proximal end portion 120 of the body. Particularly if the container 300 is sized to lie completely within the body 100 or extend to the proximal end portion 120, the retaining cap 140 and plunger 142 may be provided to provide an efficient actuation mechanism for the applicator assembly.

As shown in FIG. 2, the middle body portion 150 may be configured to have thicker walls than the proximal end portion 120. The thicker walls may resist accidental activation of the applicator by protecting the sealed distal end 310 of the container 300 from external pressure or jarring during assembly, transport, and/or prior to intended use, for example. The distal end portion 110 may be configured to taper, for example, from an optional finger flange 112 provided toward the middle body portion 150 to a neck portion 114 connected to the mounting flange 130. The finger flange 112 may provide a seat for fingers or a hand during activation of the applicator or during application of a solution, for example, to prevent slipping and/or to provide enhanced grip.

With the container 300 concentrically mounted in the body 100, as described above, and the application member 200 mounted to close off the distal end portion 110 of the body 100, a fluid chamber 160 may be formed that extends through at least a portion of the middle body portion 150 and the distal end of the body 100 between the application member 200 and the container 300. A fluid metering device, such as a pledget 170, for example, may be optionally provided in the fluid chamber 160 to further control and/or direct the flow of solution from the container 300 when the assembly 10 is in use. In accordance with another aspect of the present invention, the pledget 170 may tint the solution as the solution flows from the container 300 to the application member 200.

Activation of the applicator to release the solution may be accomplished by using fingers to pinch or pressure the applicator and/or through activation of the release mechanism 180 configured into the structure of the applicator. As shown in FIG. 2, the release mechanism 180, which may include one or more wedges formed on an interior surface of the body 100, may be configured into the fluid chamber 160 to promote the "pinching" effect of the applied compressive forces. For example, the release mechanism 180 may be configured to apply an increasing compressive force against circumferential areas of the distal end 310 of the container 300 as the container 300 is pushed from the proximal end 320. The release mechanism 180 may be formed so as to simultaneously allow circumferential areas of the distal end 310 of the container 300 to expand as the container 300 translates further into the fluid chamber 160.

The activation force may be applied against the proximal end 320 of the container 300 or the plunger 142 abutting the proximal end 320 of the container 300 in a direction along the longitudinal axis of the body 100 toward the distal end portion 110. For example, a user may activate the applicator with one hand by grasping or holding the body 100 of the applicator in the palm of the hand with the application member 200 facing down. The user may wrap four fingers circumferentially around the body 100 so that the thumb extends freely towards the proximal end 320 of the container 300. With the four fingers holding the body 100, the thumb may be used to apply the necessary force against the proximal end 320 or the plunger 142 required to overcome any optional retaining mechanism and translate the container 300 into the fluid chamber 160. The solution container 300 may be ergonomically formed with a recessed area in the proximal end 320, for example, to enhance the ability of the user to situate a thumb on the container 300 and apply the necessary force. Alternatively, a user may hold the applicator 10 in one hand and bump the proximal end 320 or the plunger 142 against the palm of the other hand, for example, or against any other suitable surface or object in order to push the container 300 into the fluid chamber 160.

The activation force applied against the proximal end 320 of the container 300 may result in compressive forces, as shown by the arrows in FIGS. 3 and 4, being applied by the release mechanism 180 along circumferential areas of the distal end 310 of the container 300. In reaction to the compressive forces, the distal end 310 of the container 300 may deform inward near the circumferential areas experiencing the compressive loads. Consequently, circumferential areas of the distal end 310 perpendicular to the applied compressive forces may be forced to deform outward (see FIG. 4). The combined inward and outward deformation of the circumferential areas of the distal end 310 may yield areas of high tensile stress in the sealing material 350 and/or the bond that seals the sealing material 350 to the container 300 along the circumferential areas of the distal end 310 substantially perpendicular to the applied compressive forces. As a result, the tensile stress may reach a point to cause a failure in the material properties of the sealing material 350 and/or the bond that seals the sealing material 350 to the container 300. The result may be a tearing of the sealing material 350 and/or a separation of the sealing material 350 from the container 300 in a manner that results in one or more gaps 355 being formed in the areas of maximum tensile stress. The gaps 355 establish a fluid communication between the interior of the container 300 and the fluid chamber 160, releasing the sealed solution into the applicator body 100. Once the seal is thus broken, positioning the applicator 10 with the application member 200 situated below the container 300 allows the solution to drain from the container 300 into the fluid chamber 160 under its own weight. Upon release of the activation force applied to the proximal end 320, the ruptured seal may remain open to permit the application member 200 to become fully engorged. Furthermore, because the seal may rupture at more than one circumferential area (e.g., at diametrical opposed circumferential areas experiencing a maximum tensile load), the flow of the solution to the application member 200 may be enhanced through creation of both a drain and a vent.

The solution may soak into, or otherwise flow through, the application material 200 at a specified volume and rate. The fluid chamber 160 may serve to accumulate and distribute the solution evenly over substantially the entire area of the application material 200. Once the application material 200 is engorged, for example, the solution may then be applied to a patient by wiping the distal surface of the application material 200 against the skin.

Figure 6A:
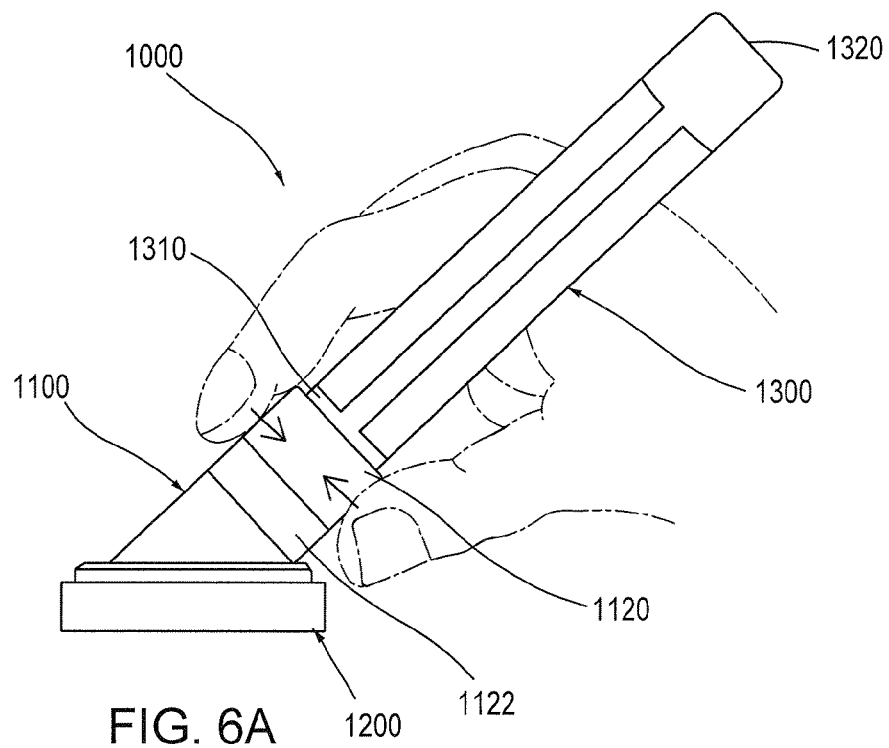
FIG. 6A is a perspective view of an antiseptic applicator shown in use, in accordance with certain aspects of the present invention.
Figure 6B:
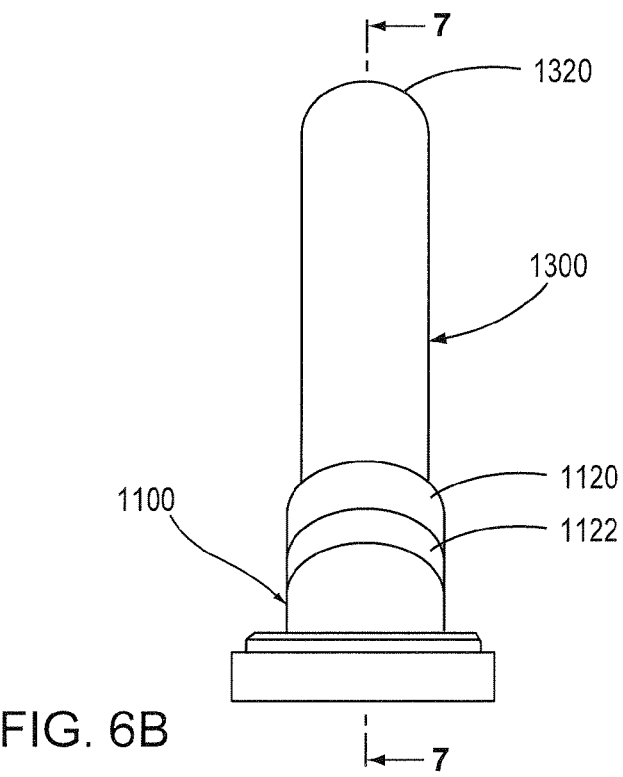
FIG. 6B is a front view of the antiseptic applicator of FIG. 6A.
Figure 7:
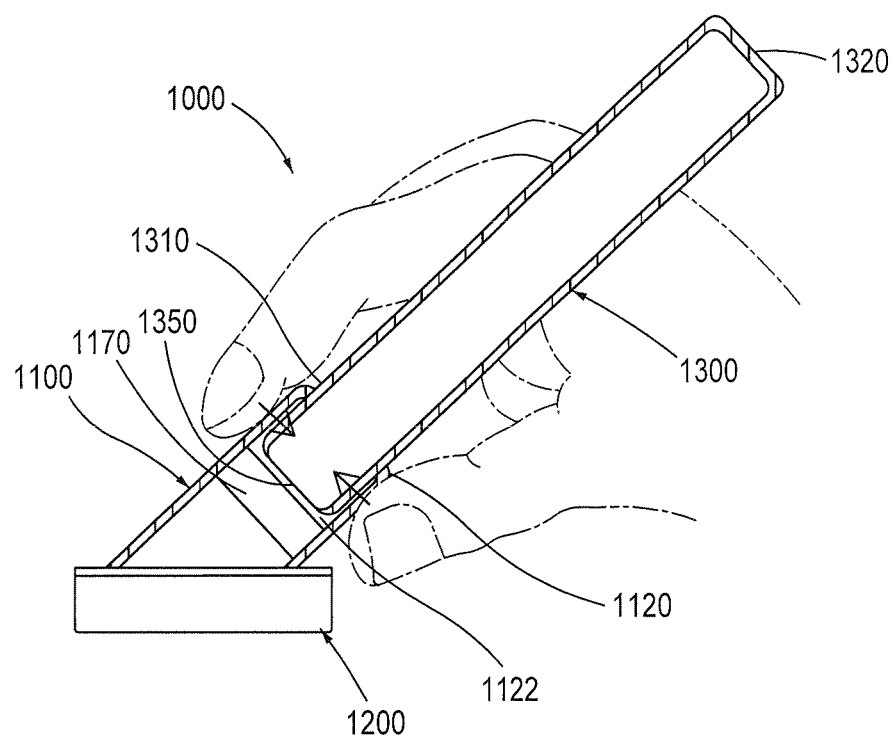
FIG. 7 is a sectional view of the antiseptic applicator shown in FIGS. 6A and 6B, in accordance with certain aspects of the present invention.

FIGS. 6A, 6B and 7 illustrate an exemplary applicator assembly 1000 in accordance with certain aspects of the present invention that functions in most respects similar to the applicator assembly 10, and, as such, a majority of the structure and functional aspects of the applicator assembly 1000 are not repeated here. The applicator assembly 1000 may include a cylindrical solution container 1300 having a distal end 1310 and a proximal end 1320, wherein the distal end 1310 is configured to connect with a cylindrical proximal end portion 1120 of a body 1100. For example, the proximal end portion 1120 may be formed to slidably accept and retain the distal end 1310, such as by press fit or through use of an adhesive. A retention shelf 1122 or suitable stops, for example, may be configured into or separately attached to the body 1100 to seat the distal end 1310 of the container in the proximal portion 1120 of the body. In accordance with another aspect of the present invention, the distal end 1310 of the container 1300 may be provided with a suitable mating feature, such as an external threading feature or a snap flange feature, for example, configured to mate respectively with an internal threading feature or a snap groove feature provided in the proximal end portion 1120 of the body 1100.

As discussed above with respect to container 300, the container 1300 may be sealed at the distal end 1310 with a sealing material 1350, such as a thin plastic or an aluminum foil, for example. The sealing material may be bonded to close the open distal end of the container 1300 so that the solution contained therein is sealed from any external contamination. The material properties and/or configuration of the sealing material 1350, as well as the type and strength of the bond between the sealing material 1350 and the container 1300, are such that application of substantially opposing compressive forces (i.e., a pinching or clamping force), applied toward the distal end 1310 of the container 1300, may force a tearing of the sealing material 1350 and/or a separation of the sealing material 1350 from the container 1300 (see, e.g., FIGS. 3 and 4).

The proximal end portion 1120 of the body 1100 may be formed of a suitable material, such as a high density polyethylene material, to provide sufficient structure for retaining the container 1300 and sufficient flexibility to permit deformation during application of a compressive force to break the seal on the container 1300. Thus, with the distal end 1310 of the container 1300 housed in the proximal end portion 1120 of the body 1100, a user may grasp the applicator 1000, as shown in FIGS. 6A and 7, and apply a compressive force by pinching the proximal end portion 1120 of the body 1100 in the area of the distal end 1310 of the container 1300. Visual and/or tactile indicators, including the shape and configuration of the proximal end portion 1120 itself, may be provided to assist the user in making the determination of where to apply pressure. The application of compressive force as illustrated in FIGS. 6A and 7 may cause the container 1300 to deform, as described above with container 300, resulting in the same or similar stress being applied to the sealing material and/or the bond of the sealing material to the container 1300 to allow a release of the solution contained therein. In accordance with another aspect of the invention, release mechanisms such as tappets or wedges, for example, may be provided on an interior surface of the proximal end portion 1120 of the body to enhance the compressive effect of the applied "pinching" force. The solution may soak into, or otherwise flow through, an application material 1200 provided at the distal end of the body 1100 for application to a patient or a surface, for example. As shown in FIG. 7, a fluid metering device, such as a pledget 1170, for example, may be optionally provided in the body 1100 to further control and/or direct the flow of solution from the container 1300 when the assembly 1000 is in use. In accordance with another aspect of the present invention, the pledget 1170 may tint the solution as the solution flows from the container 1300 to the application member 1200.

A method of manufacturing an applicator for applying a solution to a surface may comprise providing a container having a closed proximal end, an interior receptacle, and an open distal end; filling the interior receptacle with the solution to be applied; bonding a sealing material to the open distal end of the container to seal the solution in the interior receptacle of the container; providing an applicator body having a proximal end portion and a distal end portion; coupling an application material to the distal end portion; and coupling the container to the proximal end portion, wherein application of a compressive force on the distal end of the container ruptures the sealing material bond and allows the solution to flow through the body to the application material. The sealing material may be a foil material. The method may include providing the body with a release mechanism, wherein the release mechanism applies the compressive force in response to an activation force applied longitudinally against the proximal end of the container. The release mechanism may comprise at least one wedge arranged on an interior surface of the body. The method may include configuring the body with a retaining mechanism that resists separation of the container from the body. The retaining mechanism may be a tapered configuration of the proximal end portion. The retaining mechanism may be a retaining cap and plunger provided at the proximal end portion of the body to completely enclose the container in the body. The method may include configuring the body with a middle body portion connecting the proximal end portion and the distal end portion, the middle body portion having thicker walls than the proximal end portion and housing the distal end of the container. A fluid chamber may be defined between the application member and the container by the middle body portion and the distal end portion. The method may include providing a pledget in the fluid chamber.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:
1. An applicator assembly comprising:
a body having a proximal end portion, a distal end portion, and a release mechanism;
a container having a closed proximal end, an interior, an open distal end, and a sidewall, wherein the container is interoperable with the proximal end portion;

a material bonded to the open distal end and sealing the interior of the container; and an application member attached to the distal end portion, wherein the body, the container, and the release mechanism are configured to cooperate to cause deformation of at least a portion of the sidewall of the container, wherein the deformation of the at least a portion of the sidewall of the container ruptures the bond of the material such that the interior of the container is placed in fluid communication with the application member, and wherein the cooperation of the body, the container, and the release mechanism causes the deformation in response to an activation force applied longitudinally against the proximal end of the container.

2. The applicator assembly of claim 1, wherein the material is a foil material.

3. The applicator assembly of claim 1, wherein the release mechanism comprises at least one wedge arranged on an interior surface of the body.

4. The applicator assembly of claim 1, wherein the body further comprises a retaining mechanism that resists separation of the container from the body.

5. The applicator assembly of claim 4, wherein the retaining mechanism comprises a tapered configuration of the proximal end portion.

6. The applicator assembly of claim 1, wherein the body further comprises a middle body portion connecting the proximal end portion and the distal end portion, the middle body portion having thicker walls than the proximal end portion and housing the distal end of the container.

7. The applicator assembly of claim 6, further comprising a fluid chamber defined between the application member and the container by the middle body portion and the distal end portion.

8. The applicator assembly of claim 7, further comprising a pledget provided in the fluid chamber.

9. The applicator assembly of claim 1, wherein the distal end portion comprises a finger flange and a mounting flange connected by a neck section.

10. The applicator assembly of claim 1, wherein application of the compressive force creates a tensile stress in the bond which ruptures the seal along circumferential areas of the distal end substantially perpendicular to the circumferential areas of the applied compressive force.

11. The applicator assembly of claim 1, further comprising a retaining cap and plunger provided at the proximal end portion of the body to completely enclose the container in the body.

12. The applicator assembly of claim 1, wherein the body further comprises a sidewall, and wherein the release mechanism comprises at least one wedge arranged on an interior surface of the sidewall of the body.

13. A method of manufacturing an applicator for applying a solution to a surface comprising:

providing a container having a closed proximal end, an interior receptacle, an open distal end, and a sidewall;

filling the interior receptacle with the solution to be applied;

bonding a sealing material to the open distal end of the container to seal the solution in the interior receptacle of the container;

providing an applicator body having a proximal end portion, a distal end portion, and a release mechanism;

coupling an application material to the distal end portion; and inserting the container into the proximal end portion, wherein the body, the container, and the release mechanism are configured to cooperate to cause deformation of at least a portion of the sidewall of the container, wherein the deformation of the at least a portion of the sidewall of the container ruptures the sealing material bond and allows the solution to flow through the body to the application material, and wherein the cooperation of the body, the container, and the release mechanism cause the deformation in response to an activation force applied longitudinally against the proximal end of the container.

14. The method of claim 13, wherein the sealing material is a foil material.

15. The method of claim 13, wherein the release mechanism comprises at least one wedge arranged on an interior surface of the body.

16. The method of claim 13, further comprising: configuring the body with a retaining mechanism that resists separation of the container from the body.

17. The method of claim 16, wherein the retaining mechanism is a tapered configuration of the proximal end portion.

18. The method of claim 16, wherein the retaining mechanism is a retaining cap and plunger provided at the proximal end portion of the body to completely enclose the container in the body.

19. The method of claim 13, further comprising: configuring the body with a middle body portion connecting the proximal end portion and the distal end portion, the middle body portion having thicker walls than the proximal end portion and housing the distal end of the container.

20. The method of claim 19, wherein a fluid chamber is defined between the application member and the container by the middle body portion and the distal end portion.

21. The method of claim 20, further comprising: providing a pledget in the fluid chamber.

22. The method of claim 13, wherein the body further comprises a sidewall, and wherein the release mechanism comprises at least one wedge arranged on an interior surface of the sidewall of the body.

* * * * *